US012797135B2

(12) United States Patent
Frushour

(10) Patent No.: US 12,797,135 B2
(45) **Date of Patent: *Nov. 17, 2026**

(54) LOCALIZATION SYSTEMS AND METHODS OF USE

(71) Applicant: Covidien LP, Mansfield, MA (US)

(72) Inventor: Scott E. M. Frushour, Boulder, CO (US)

(73) Assignee: Covidien LP, Mansfield, MA (US)

( * ) Notice: Subject to any disclaimer, the term of this patent is extended or adjusted under 35 U.S.C. 154(b) by 125 days.

This patent is subject to a terminal disclaimer.

(21) Appl. No.: 18/210,752

(22) Filed: Jun. 16, 2023

(65) Prior Publication Data

US 2023/0338092 A1 Oct. 26, 2023

Related U.S. Application Data

(63) Continuation of application No. 16/715,086, filed on Dec. 16, 2019, now Pat. No. 11,690,679.

(Continued)

(51) Int. Cl.

*A61B 34/20* (2016.01)
*A61B 17/00* (2006.01)

(Continued)

(52) U.S. Cl.

CPC .... *A61B 34/20* (2016.02); *A61B 2017/00004* (2013.01); *A61B 2017/0023* (2013.01); *A61B 17/00234* (2013.01); *A61B 2017/00809* (2013.01); *A61B 2018/00595* (2013.01); *A61B 2018/1253* (2013.01); *A61B 2018/126* (2013.01); *A61B 2034/2051* (2016.02); *A61B 2034/2061* (2016.02); *A61B 34/30* (2016.02); *A61B 2090/3735* (2016.02); *A61B 2090/374* (2016.02); *A61B 2090/376* (2016.02);

(Continued)

(58) Field of Classification Search

CPC ...... A61B 2090/3735; A61B 2090/374; A61B 2090/376; A61B 2090/3762; A61B 2090/378

See application file for complete search history.

(56) References Cited

U.S. PATENT DOCUMENTS 5,242,456 A 9/1993 Nash et al.
5,415,666 A 5/1995 Gourlay et al.

(Continued)

FOREIGN PATENT DOCUMENTS

CN 104321014 A 1/2015
CN 106214202 A 12/2016

(Continued)

OTHER PUBLICATIONS

International Search Report corresponding to the International Application No. PCT/US2017/014038, dated May 4, 2017; 5 pages.

(Continued)

*Primary Examiner* — Thomas McEvoy

(74) *Attorney, Agent, or Firm* — Weber Rosselli & Cannon LLP

(57) ABSTRACT

A method for localizing a nodule of a patient includes inserting a delivery tool into tissue of a patient, such as lung tissue, releasing the magnetic fiducial into or adjacent a nodule from the delivery tool, and locating the magnetic fiducial with a localization tool.

20 Claims, 4 Drawing Sheets

Related U.S. Application Data

(60) Provisional application No. 62/800,665, filed on Feb. 4, 2019, provisional application No. 62/789,604, filed on Jan. 8, 2019.

(51) Int. Cl.
*A61B 18/00* (2006.01)
*A61B 18/12* (2006.01)
*A61B 34/30* (2016.01)
*A61B 90/00* (2016.01)

(52) U.S. Cl.
CPC . *A61B 2090/3762* (2016.02); *A61B 2090/378* (2016.02); *A61B 2090/3958* (2016.02); *A61B 2090/3966* (2016.02)

(56) References Cited

U.S. PATENT DOCUMENTS

| | | | |
|---|---|---|---|
| 5,509,923 A | 4/1996 | Middleman et al. | |
| 5,512,037 A | 4/1996 | Russell et al. | |
| 6,173,715 B1 | 1/2001 | Sinanan et al. | |
| 8,187,315 B1 | 5/2012 | Clauson et al. | |
| 9,463,003 B2 | 10/2016 | Gordin et al. | |
| 10,231,718 B2 | 3/2019 | Ciulla et al. | |
| 10,342,540 B2 | 7/2019 | Smith et al. | |
| 10,537,316 B2 | 1/2020 | Smith et al. | |
| 11,690,679 B2 | 7/2023 | Frushour | |
| 2004/0176797 A1* | 9/2004 | Opolski | A61B 17/12022 606/213 |
| 2008/0039676 A1 | 2/2008 | Fischell et al. | |
| 2008/0221599 A1 | 9/2008 | Starksen | |
| 2011/0160129 A1 | 6/2011 | Imran | |
| 2011/0282144 A1 | 11/2011 | Gettman | |
| 2012/0289776 A1 | 11/2012 | Keast et al. | |
| 2014/0228943 A1* | 8/2014 | Stigall | A61B 5/6852 623/2.11 |
| 2014/0257238 A1 | 9/2014 | Imran | |
| 2015/0051642 A1 | 2/2015 | Broom et al. | |
| 2017/0035407 A1 | 2/2017 | Duan et al. | |
| 2017/0209132 A1 | 7/2017 | Bhatt et al. | |

FOREIGN PATENT DOCUMENTS

| | | | |
|---|---|---|---|
| DE | 102005002944 | A1 | 7/2006 |
| DE | 102010010478 | A1 | 9/2011 |
| EP | 1598020 | A1 | 11/2005 |
| EP | 2578167 | A1 | 4/2013 |
| JP | 2004321482 | A | 11/2004 |
| JP | 2005103107 | A | 4/2005 |
| JP | 2008142516 | A | 6/2008 |
| JP | 2008155006 | A | 7/2008 |
| JP | 4320207 | B2 | 8/2009 |
| JP | 4472680 | B2 | 6/2010 |
| WO | 0051514 | A1 | 9/2000 |
| WO | 2009034922 | A1 | 3/2009 |
| WO | 2012154845 | A1 | 11/2012 |
| WO | 2014055193 | A1 | 4/2014 |
| WO | 2018227592 | A1 | 12/2018 |

OTHER PUBLICATIONS

Australian Examination Report issued in corresponding Australian Application No. 2017209092, dated Nov. 30, 2018; 5 pages.

International Search Report and Written Opinion of the International Searching Authority, dated Feb. 20, 2019, corresponding to counterpart International Application No. PCT/US2018/059867; 15 total pages.

European Search Report dated Jun. 5, 2020, corresponding to counterpart European Application No. 20150452.9; 7 pages.

Office Action issued in corresponding Chinese application 202010015953.0 mailed Dec. 13, 2023, together with machine translated English language translation (10 pages).

* cited by examiner

LOCALIZATION SYSTEMS AND METHODS OF USE

CROSS-REFERENCE TO RELATED APPLICATIONS

This application is a continuation of U.S. patent application Ser. No. 16/715,086, filed on Dec. 16, 2019, which claims the benefit of the filing date of provisional U.S. Patent Application No. 62/789,604, filed on Jan. 8, 2019, and the filing date of provisional U.S. Patent Application No. 62/800,665, filed on Feb. 4, 2019.

INTRODUCTION

The present disclosure relates to localization systems and, more specifically, to localization systems for localizing lung nodules and methods of using the localization systems.

BACKGROUND

In lung resection of smaller nodules, it is becoming common practice to use localization tools to aid the surgical team in effective resection of smaller nodules that may not be palpable with current techniques. Several preoperative and intraoperative techniques are presently being used for nodule localization. One of these techniques utilizes small fiducials that are guided to a position adjacent a lung nodule using medical imaging, such as computed tomography. However, sometimes, small fiducials cannot be easily located intraoperatively without the use of X-ray, digital palpation and/or a robot. Therefore, there is a continuing need for better and more cost-effective methods for nodule localization.

SUMMARY

Provided in accordance with the present disclosure is a method for localizing a nodule of a patient. The method includes inserting a delivery tool into a patient. The delivery tool carries a magnetic fiducial, which is released from the delivery tool into or adjacent a nodule. The magnetic fiducial is located with a localization tool.

In some methods, locating the magnetic fiducial may include guiding a magnetic portion of the localization tool toward the magnetic fiducial.

Some methods may further include locking the magnetic portion of the localization tool onto the magnetic fiducial.

In some methods, releasing the magnetic fiducial may include advancing a pusher of the delivery tool, thereby separating the magnetic fiducial from a permanent magnet of the delivery tool.

In some methods, the magnetic fiducial may include a radiopaque material visualized using an imaging system during insertion of the delivery tool.

In another aspect of the present disclosure, a localization system is provided and includes a magnetic fiducial, a delivery tool configured to deploy the magnetic fiducial therefrom, and a localization tool having a magnetic portion configured to attract the magnetic fiducial.

In some aspects, the magnetic portion of the localization tool may be configured to selectively lock onto the magnetic fiducial.

In some aspects, the delivery tool may include a housing configured for receipt of the magnetic fiducial, and a pusher axially movable through the housing and configured to release the magnetic fiducial from the housing.

In some aspects, the delivery tool may further include a permanent magnet disposed within the housing and adjacent the magnetic fiducial.

In some aspects, the permanent magnet may be disposed proximally of the magnetic fiducial. The permanent magnet may have a distal end having a north polarity or a south polarity, and the magnetic fiducial may have a proximal end having the other of the north polarity or the south polarity.

In some aspects, the magnetic fiducial may include a radiopaque material.

Further details and aspects of exemplary embodiments of the present disclosure are described in more detail below with reference to the appended figures.

BRIEF DESCRIPTION OF THE DRAWINGS

Various aspects and features of the present disclosure are described hereinbelow with references to the drawings, wherein.

DETAILED DESCRIPTION

Figure 1:
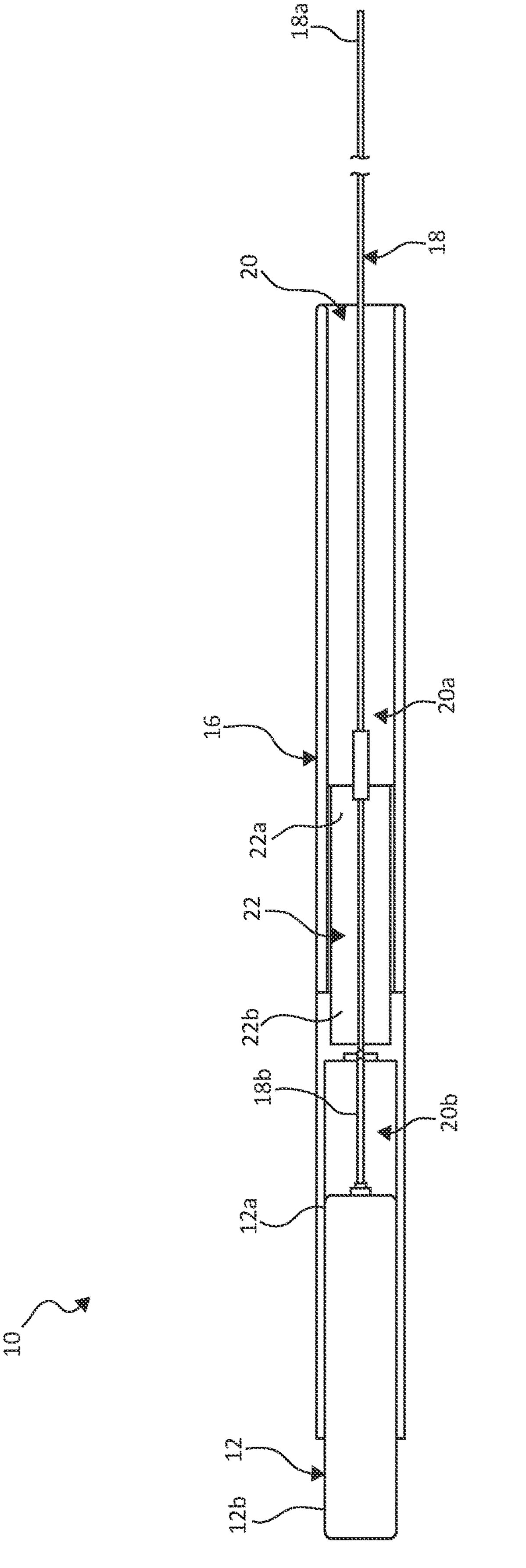
FIG. 1 is a side, cross-sectional view of an exemplary embodiment of a delivery tool and a magnetic fiducial marker shown in a partially-deployed state relative to the delivery tool.

The present disclosure is directed to a localization system and method for localization of a nodule in a lung. The system includes a magnetic fiducial marker, a delivery tool for delivering the magnetic fiducial marker to the nodule in the lung, and a localization tool for locating the magnetic fiducial marker. The delivery tool has a flexible body navigable through the lungs, airways, and/or other natural lumens of the body, and an end effector disposed at a distal end of the flexible body. The end effector has a magnetic portion magnetically attracted to the magnetic fiducial marker to assist in delivering the magnetic fiducial marker into the body in the pre-operative setting. Using X-ray, ultrasound, tomography, or any other suitable imaging system or navigation, the magnetic fiducial marker is placed in or adjacent to the nodule. Multiple fiducial markers may be placed around the nodule to aid in triangulation. Other types of imaging technology may be utilized, such as computed tomography (CT), magnetic resonance imaging (MRI), fluoroscopy, thermography, ultrasound, optical coherence tomography (OCT), thermal imaging, impedance imaging, laser imaging, or nanotube X-ray imaging. Other navigation techniques may be utilized, including the use of electromagnetic fields, virtual bronchoscopy, AI-enabled navigation, machine learning-enabled navigation, or fiber optic position and shape sensing devices such as Fiber Bragg Gratings, Raleigh scattering, Raman scattering, Brillouin scattering and Fluorescence scattering.

The magnetic portion of the localization tool is navigated through the chest during the preoperative or intraoperative portion of therapy until the magnetic fiducial marker is located, whereupon the magnetic portion of the localization tool is attracted to the deployed magnetic fiducial marker through the pleural surface and parenchymal tissue of the lung. After the magnetic portion of the localization tool has been attracted to the magnetic fiducial marker, the removal of the nodule along with the magnetic fiducial marker may begin.

It is contemplated that the methods described herein may be applied in various surgical procedures, such as tissue-sparing colorectal surgery, and to treat various diseases such as pancreatic, urologic, uterine, gastric or esophageal cancers.

Embodiments of the present disclosure will now be described in detail with reference to the drawings in which like reference numerals designate identical or corresponding elements in each of the several views. As is understood in the art, the term “clinician” refers to a doctor, a physician, a nurse, a bronchoscopist, or any other care provider or support personnel. Further, as is understood in the art the term “proximal” refers to the portion of the localization system, or any component thereof, that is closest to the clinician and the term “distal” refers to the portion of the localization system, or any component thereof, that is furthest from the clinician.

Figure 2:
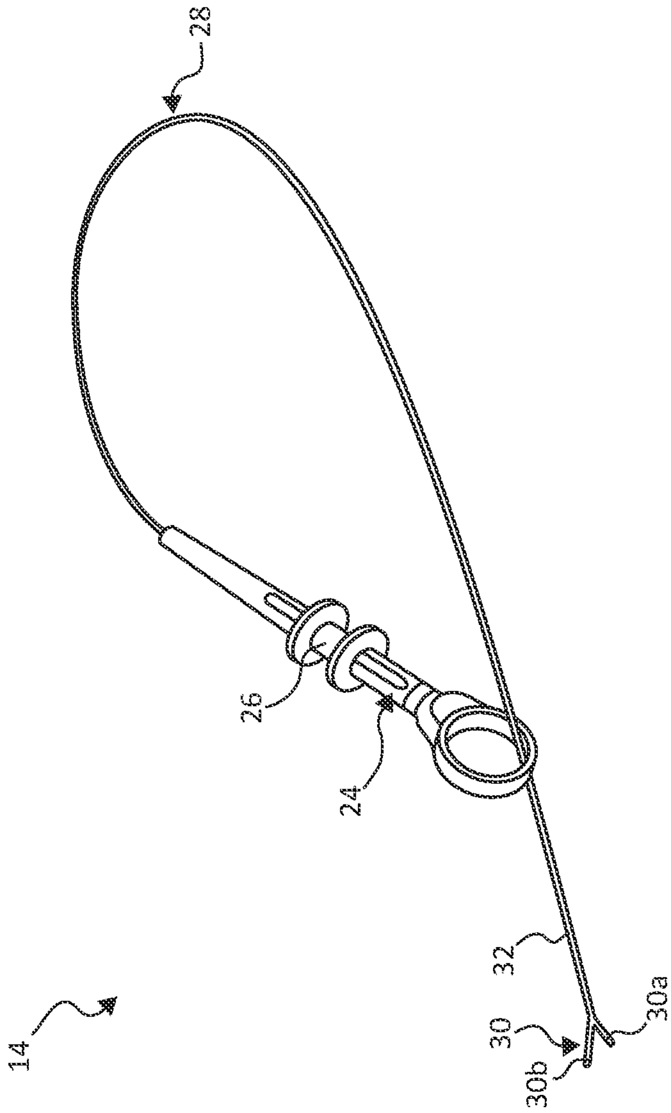
FIG. 2 is a perspective view of an exemplary embodiment of a localization tool for use with the delivery tool and the magnetic fiducial marker shown in FIG. 1.

With reference to FIGS. 1 and 2, a localization system is illustrated and generally includes a hand-held or robotically-operated delivery tool 10, a magnetic fiducial marker 12 selectively disposed within and deployable from the delivery tool 10, and a localization tool 14 (FIG. 2) for locating, using the forces of magnetic attraction, the magnetic fiducial marker 12 within the lung.

With reference to FIG. 1, the delivery tool 10 includes a catheter, such as, for example, an elongate housing 16, and a pusher 18 slidably received in the elongate housing 16. The elongate housing 16 may be fabricated from a flexible material and have a diameter (e.g., about 0.5 mm to about 2 mm, and in some aspects, about 3.3 mm) sufficiently small to permit navigation through the passageways of the lung. The pusher 18 may be configured as a rod having a proximal end 18*a* to be manipulated by a clinician or robot, and a distal end 18*b* disposed within the elongate housing 16 adjacent a proximal end 12*a* of the magnetic fiducial marker 12. Since the distal end 18*b* of the pusher 18 abuts the proximal end 12*a* of the magnetic fiducial marker 12, distal movement of the pusher 18 through the elongate housing 16 advances the magnetic fiducial marker 12 out of the delivery tool 10.

The elongate housing 16 of the delivery tool 10 defines a longitudinally-extending passageway 20 therethrough. The passageway 20 has a proximal section 20*a* having a magnet 22, such as, for example, a permanent magnet received therein, and a distal section 20*b* having the magnetic fiducial marker 12 removably received therein. The permanent magnet 22 of the delivery tool 10 may be axially restrained within the proximal section 20*a* of the passageway 20 and function to maintain the magnetic fiducial marker 12 within the distal section 20*b* of the passageway 20. In particular, the permanent magnet 22 has a distal end 22*b* having a north polarity or a south polarity, whereas the magnetic fiducial marker 12 has a proximal end 12*a* having an opposite polarity as the distal end 22*b* of the permanent magnet 22. When the magnetic fiducial marker 12 is received in the distal section 20*b* of the passageway 20, the proximal end 12*a* of the magnetic fiducial marker 12 is disposed adjacent the distal end 22*b* of the permanent magnet 22, whereby the magnetic attraction between the permanent magnet 22 and the magnetic fiducial marker 12 maintains the magnetic fiducial marker 12 within the delivery tool 10 until a threshold, distally-oriented force is exerted on the magnetic fiducial marker 12 via the pusher 16.

In embodiments, the permanent magnet 22 may have a dynamic component allowing for the adjustment of its polarity and/or magnetic strength. Alternately, instead of being axially restrained within the elongate housing 16, the permanent magnet 22 may be slidable within the elongate housing 16 to help position the magnetic fiducial marker 12 in tissue and/or to retrieve the magnetic fiducial marker 12 back into the elongate housing 16. In this alternate embodiment, a secondary pusher (not shown) may be provided for adjusting the axial position of the permanent magnet 22 relative to the elongate housing 16. In aspects, the delivery tool may be a percutaneous needle or an endobronchial catheter and may be used in open, laparoscopic/VATS, or robotic access methods. In some aspects, the delivery tool may be an endoluminal catheter.

With continued reference to FIG. 1, the magnetic fiducial marker 12 has a cylindrical or rod-like configuration having a diameter of about 0.5 mm to about 1.5 mm (and in some aspects about 0.25 mm) and a length of about 3 mm to about 6 mm (and in some aspects about 2.8 mm). In embodiments, the magnetic fiducial marker 12 may have a diameter of about 1 mm or less and a length of about 5 mm. In embodiments, the magnetic fiducial marker 12 may assume any suitable shape, such as, for example, disc-shaped, spherical, rectangular, star-shaped, or the like. The magnetic fiducial marker 12 may be made of, coated with, or contain neodymium or any other suitable magnetic element with strong gauss properties, such that the magnetic fiducial marker 12 can be attracted to other magnetic elements from long distances. Due to the strength of the magnetic properties of the magnetic fiducial marker 12, the localization tool 14 (FIG. 2) may be able to locate the magnetic fiducial marker 12 through extremely thick tissue planes. The magnetic fiducial marker 12 may also be radiopaque (e.g., the fiducial markers may have a radiopaque coating) so that it can be seen in stereotactic body radiation therapy or surgical procedures with imaging systems such as X-ray, cone beam CT, CAT, fluoroscopy, etc.

The magnetic fiducial marker 12 may have fixation elements, such as, for example, wires or barbs (not shown) extending therefrom to limit migration in the airways or parenchymal tissue. The fixation elements may be made from ferrous or non-ferrous materials including plastics, rubbers, metals etc. In certain embodiments, the fixation elements may be fabricated from absorbable material that allows for biological ingrowth to capture the fixation elements. For example, the fixation elements may be fabricated from or coated with poly-glycolic acid (PGA) or bio-scaffold materials like collagen matrices. In aspects, the magnetic fiducial marker 12 may be hollow and configured to store therein a chemical payload to allow for localized identification with, for example, white light, NIR, and/or spectral imaging systems. The chemical payload may include indocyanine green, methylene blue, carmine blue, or fluorophores and may be designed to be released from the magnetic fiducial marker 12 at a given rate, all at once, or in the presence of a magnetic field. For example, the magnetic fiducial marker 12 may be equipped with a valve configured to selectively release the chemical payload.

With reference to FIG. 2, the localization tool 14 of the localization system is configured to locate the magnetic fiducial marker 12 or a plurality of magnetic fiducial markers 12 after the magnetic fiducial marker 12 has been placed in a nodule. The localization tool 14 may be reusable with the assistance of a plastic surgical condom (not shown), or be disposable. The localization tool 14 may be hand-operated or be attached to a robotic arm 1003 (FIG. 4) and includes a housing 24, an actuator 26 slidably coupled to the housing 24, a flexible shaft 28 extending from the housing 24, and a magnetic portion 30 coupled to a distal end 32 of the flexible shaft 28. The flexible shaft 28 may have a diameter of about 5 mm or less and be sufficiently flexible to allow for manipulation with traditional surgical instruments. The flexible shaft 28 may be replaced with a rigid shaft for use in open, laparoscopic/VATS, or robotic procedures.

The actuator 26 is configured to actuate a push-wire (not shown) that extends through the flexible shaft 28 and is coupled to the magnetic portion 30. Movement of the push-wire, via a sliding actuation of the actuator 26, is configured to actuate the magnetic portion 30. Actuation of the magnetic portion 30 may include an opening or closing of the magnetic portion 30. In other embodiments, actuation of the magnetic portion 30 may include distal advancement of the magnetic portion 30 from the distal end 32 of the flexible shaft 28. In other embodiments, the magnetic portion 30 may be a solid piece of magnetic material. In aspects, the magnetic portion 30 may include electromagnetic properties and be energized via a power source to enhance the power (gauss) of the magnetic field and/or focus the magnetic field.

The magnetic portion 30 of the localization tool 14 may be made of, coated with, or contain neodymium or any other suitable magnetic element with strong gauss properties, such that the magnetic portion 30 will be attracted to the magnetic fiducial marker 12 from long distances. The magnetic portion 30 of the localization tool 14 would be attracted to the bronchoscopically placed magnetic fiducial marker 12, enabling a very precise visualization of where the nodule is for the surgeon performing the resection. The magnetic portion 30 may include a pair of opposing jaw members 30*a*, 30*b* configured to move between closed and open configurations in response to movement of the push-wire. In embodiments, the magnetic portion 30 may be configured as a hollow cylinder dimensioned to capture at least a portion of the magnetic fiducial marker 12 therein. In other embodiments, the magnetic portion 30 may be a solid piece of magnetic material. Jaw members 30*a*, 30*b* may be energized with monopolar or bipolar electrocautery for demarcating attraction points on the pleural surface of the lung. In aspects, instead of or in addition to making portion 30 magnetic, the portion 30 may have an adhesive coating with a bond strength selected to lock the localization tool 14 onto a magnetic or non-magnetic fiducial marker 12.

It may be beneficial for the magnetic portion 30 to be removable from the distal end 32 of the flexible shaft 28 and/or rotatable relative to the distal end 32 of the flexible shaft 28. As such, if a particular pole (e.g., the north pole) of the magnetic fiducial marker 12 is more accessible to the localization tool 14, the magnetic portion 30 of the localization tool 14 may be rotated to distally-orient the magnetically attracted pole (e.g., the south pole) of the magnetic portion 30. In this embodiment, the localization tool 14 may include another magnet (not shown) fixed therein to assist in maintaining the magnetic portion 30 secured to the localization tool 14. Alternately, if the magnetic fiducial marker 12 is always inserted with the south pole facing proximally, then the magnetic portion 30 of the localization tool 14 should always have its north pole facing distally and vice-versa.

In operation, marking of a lung nodule may be performed during pre-operative navigational bronchoscopy using manual or robotic access methods. In some instances, the localization system may be used for percutaneous marking of a tumor under CT or fluoroscopy or intraoperatively using a navigation system or other guidance. In aspects, the localization system may be used to mark nodules in any suitable tissue or organ.

Figure 3:
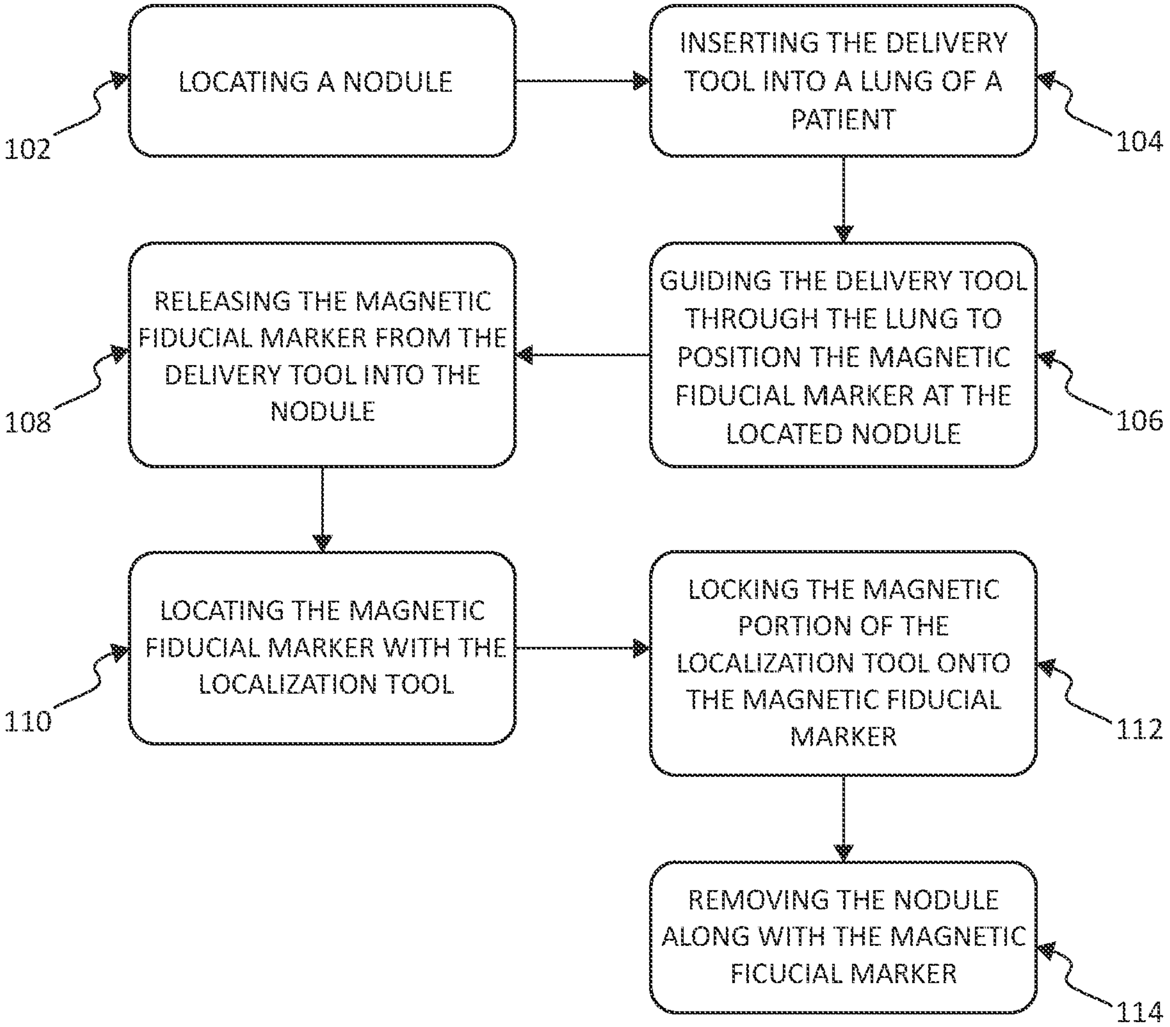
FIG. 3 is a flow chart illustrating a method of using the localization system of FIGS. 1 and 2.

In a first step 102, as shown in FIG. 3, a nodule is located using, for example, x-ray, ultrasound, tomography, or any other suitable imaging system. At a second step 104, the delivery tool 12, preloaded with the magnetic fiducial marker 12, is inserted into a lung of a patient using endobronchial or percutaneous access. At a third step 106, the delivery tool 10 is guided through the lung to position the magnetic fiducial marker 12 at the location of the nodule identified in step 102.

At a fourth step 108, the magnetic fiducial marker 12 is released from the delivery tool 10 into the nodule. The magnetic fiducial marker 12 is released from the delivery tool 12 by advancing the pusher 18 of the delivery tool 12 through the passageway 20 of the elongate housing 16, thereby overcoming the magnetic attraction between the magnetic fiducial marker 12 and the permanent magnet 22 of the delivery tool 12.

At a fifth step 110, the magnetic fiducial marker 12 is located with the localization tool 14 in the preoperative or intraoperative environment. In particular, the shaft 28 of the localization tool 14 is guided toward the magnetic fiducial marker 12 by the magnetic attraction between the magnetic portion 30 of the localization tool 14 and the magnetic fiducial marker 12 and/or utilizing imaging guidance. At a sixth step 112, upon the magnetic portion 30 of the localization tool 14 reaching the magnetic fiducial marker 12 fixed in the nodule, the magnetic portion 30 locks onto the magnetic fiducial marker 12 via the magnetic attraction therebetween and/or the jaw members 30*a*, 30*b* of the magnetic portion 30 clamping the magnetic fiducial marker 12. The flexible shaft 28 of the localization tool 14 extends from the attached magnetic fiducial marker 12, through a pleural portion of the patient, and to or out of the skin of the patient via an open incision or a trocar. In aspects, the flexible shaft 28 may extend through the intercostal space, the chest cavity, or thorax of the patient.

At a seventh step 114, after locking the magnetic portion 30 of the localization tool 14 to the magnetic fiducial marker 12, the removal of the nodule along with the magnetic fiducial marker 12 would begin.

In an alternate method, the clinician may place three or more magnetic fiducial markers 12 in airways that correspond to the oncologically appropriate margin and then the localization tool 14 could be used for outlining the margin limits for the appropriate resection.

In an alternate embodiment, the magnetic portion 30 of the localization tool 14 may have a dynamically controlled magnetic field to better control the degree of magnetic attraction between the magnetic portion 30 and the magnetic fiducial marker 12. The magnetic portion 12 may be an electromagnet having an externally controlled set-point, allowing the clinician to adjust the appropriate amount of gauss required for the procedure. In other instances, it may be advantageous to direct the emitted magnetic field to an angle away from the cylinder or distally away from the localization tool 14. An electromagnetic field coupled with an external adjusting tool could also be used for this in conjunction with the magnetic portion 30 by having a perpendicularly aligned electromagnetic element or a multi-poled electromagnetic element installed at the distal end 32 of the localization tool 14. This would help drive the magnetic portion 30 and the magnetic fiducial marker 12 together.

In yet another embodiment, the localization tool 14 could be made similar to an intraoperative ultrasound butterfly that can be grasped by a traditional surgical instrument. In this scenario, the localization tool 14 may be freely manipulated inside the body and reduce the operative burden of consuming a trocar or port. A wire may be included for powering and controlling an electromagnetic element.

Figure 4:
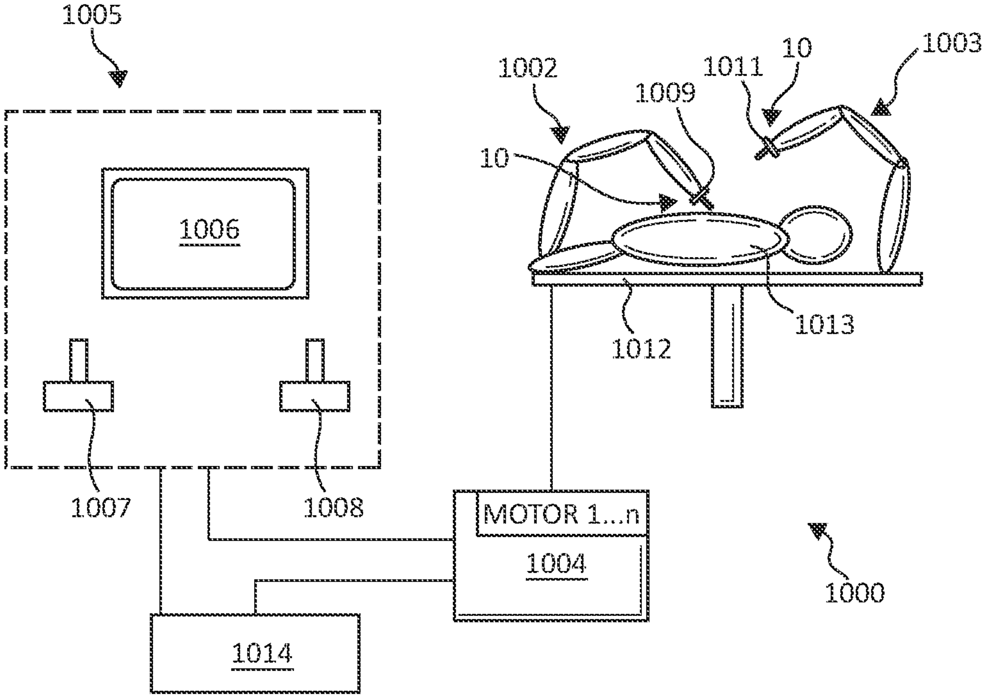
FIG. 4 is a schematic illustration of a robotic surgical system configured for use in accordance with the present disclosure.

Referring to FIG. 4, a medical work station is shown generally as robotic system or work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, the delivery tool 10 (FIG. 1) and the localization tool 14 (FIG. 2), respectively, in accordance with any one of several embodiments disclosed herein.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the delivery tool 10 and the localization tool 14, execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of the localization system. Medical work station 1000 may also include more than two robot arms 1002, 1003, the additional robot arms likewise being connected to control device 1004 and being telemanipulatable by means of operating console 1005. Medical work station 1000 may include a database 1014, in particular coupled to with control device 1004, in which are stored, for example, pre-operative data from patient/living being 1013 and/or anatomical atlases.

Reference is made herein to U.S. Pat. No. 8,828,023, the entire content of which is incorporated herein by reference, for a more detailed description of the construction and operation of an exemplary robotic surgical system.

When the localization tool 14 is operably coupled to the robotic arm 1003 (FIG. 4) of the robotic surgical system 1000, the robotic arm 1003 may be programed to have reduced strength enabling localization of the nodule. In other aspects, a magnetometer may be incorporated into the robotic arm 1003 and provide the clinician with an audible or visual indication of when the nodule or lesion is reached and potentially pin-point the nodule or lesion on an augmented overlay using robotic positioning data.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A delivery tool for deploying a fiducial within a patient, the delivery tool comprising:
- a catheter including a housing, the housing defining a longitudinally-extending passageway, the longitudinally-extending passageway having a proximal portion and a distal portion, the distal portion of the longitudinally-extending passageway configured to removably receive a fiducial;
- an axial restraining member separating the proximal portion of the longitudinally-extending passageway from the distal portion of the longitudinally-extending passageway;
- a permanent magnet axially restrained by the axial restraining member within the proximal portion of the longitudinally-extending passageway, wherein a magnetic attraction between the permanent magnet and the fiducial maintains the fiducial within the distal portion of the longitudinally-extending passageway during insertion of the delivery tool into a patient; and
- a pusher rod axially movable through the catheter, the permanent magnet, and the axial restraining member, the pusher rod configured to exert a threshold, distally-oriented force on the fiducial to overcome the magnetic attraction between the permanent magnet and the fiducial, thereby deploying the fiducial from the delivery tool.

2. The delivery tool according to claim 1, wherein the delivery tool is configured to be coupled to a robot arm of a robotic surgical system for manipulation of the delivery tool by the robot arm.

3. The delivery tool according to claim 1, wherein the fiducial includes indocyanine green configured to be released from the fiducial for localizing a target within the patient.

4. The delivery tool according to claim 1, wherein the housing has an outer diameter of between about 0.5 mm and about 2 mm.

5. The delivery tool according to claim 1, wherein the delivery tool is configured to deploy the fiducial within a lung of the patient.

6. The delivery tool according to claim 1, wherein the pusher rod is configured to be moved through the delivery tool by a robot arm of a robotic surgical system.

7. A delivery tool for deploying a fiducial within a patient, the delivery tool comprising:
- a catheter including a housing, the housing defining a longitudinally-extending passageway configured to removably receive a fiducial;
- a magnet configured to maintain the fiducial within a distal portion of the longitudinally-extending passageway during insertion of the delivery tool into a patient;
- an axial restraining member in the longitudinally-extending passageway separating a proximal portion of the longitudinally-extending passageway from a distal portion of the longitudinally-extending passageway and configured to restrain the magnet in the proximal portion of the longitudinally-extending passageway; and
- a pusher rod axially movable through the catheter, the magnet, and the axial restraining member, the pusher rod configured to deploy the fiducial from the delivery tool.

8. The delivery tool according to claim 7, wherein the magnet is a permanent magnet.

9. The delivery tool according to claim 7, wherein the delivery tool is configured to be coupled to a robot arm of a robotic surgical system for manipulation of the delivery tool by the robot arm.

10. The delivery tool according to claim 7, wherein the fiducial includes a chemical configured to be released from the fiducial for localizing a target within the patient.

11. The delivery tool according to claim 7, wherein the fiducial includes indocyanine green configured to be released from the fiducial for localizing a target within the patient.

12. The delivery tool according to claim 7, wherein the housing has an outer diameter of between about 0.5 mm and about 2 mm.

13. The delivery tool according to claim 7, wherein the delivery tool is configured to deploy the fiducial within a lung of the patient.

14. The delivery tool according to claim 7, wherein the pusher rod is configured to be moved through the delivery tool by a robot arm of a robotic surgical system.

15. A delivery tool for deploying a fiducial within a patient, the delivery tool comprising:

a catheter including a housing, the housing defining a longitudinally-extending passageway configured to removably receive a fiducial;

a permanent magnet disposed within the longitudinally-extending passageway and configured to maintain the fiducial within the longitudinally-extending passageway during insertion of the delivery tool into a patient;

an axial restraining member in the longitudinally-extending passageway separating a proximal portion of the longitudinally-extending passageway from a distal portion of the longitudinally-extending passageway and configured to restrain the permanent magnet in the proximal portion of the longitudinally extending passageway; and a pusher rod axially movable through the delivery tool, the permanent magnet, and the axial restraining member and configured to exert a threshold force on the fiducial to deploy the fiducial from the delivery tool.

16. The delivery tool according to claim 15, wherein the delivery tool is configured to be coupled to a robot arm of a robotic surgical system for manipulation of the delivery tool by the robot arm.

17. The delivery tool according to claim 15, wherein the fiducial includes a chemical configured to be released from the fiducial for localizing a target within the patient.

18. The delivery tool according to claim 15, wherein the fiducial includes indocyanine green configured to be released from the fiducial for localizing a target within the patient.

19. The delivery tool according to claim 15, wherein the housing has an outer diameter of between about 0.5 mm and about 2 mm.

20. The delivery tool according to claim 15, wherein the delivery tool is configured to deploy the fiducial within a lung of the patient.

* * * * *